US008507430B2

(12) United States Patent
Ellsworth

(10) Patent No.: US 8,507,430 B2
(45) Date of Patent: Aug. 13, 2013

(54) METHODS FOR ADMINISTERING FGF18

(75) Inventor: Jeff L. Ellsworth, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 296 days.

(21) Appl. No.: 12/104,285

(22) Filed: Apr. 16, 2008

(65) Prior Publication Data
US 2008/0193425 A1 Aug. 14, 2008

Related U.S. Application Data

(63) Continuation of application No. 10/680,673, filed on Oct. 7, 2003, now abandoned.

(60) Provisional application No. 60/416,670, filed on Oct. 7, 2002.

(51) Int. Cl.
A61K 38/18 (2006.01)
A61K 31/728 (2006.01)
C07K 14/50 (2006.01)

(52) U.S. Cl.
USPC ............................ 514/9.1; 514/17.1; 424/484

(58) Field of Classification Search
None
See application file for complete search history.

(56) References Cited

U.S. PATENT DOCUMENTS

| | | | |
|---|---|---|---|
| 4,530,840 A | 7/1985 | Tice et al. ...................... 514/179 |
| 4,636,524 A | 1/1987 | Balazs et al. ................... 514/781 |
| 5,116,753 A | 5/1992 | Beattie et al. | |
| 5,191,067 A | 3/1993 | Lappi et al. | |
| 5,308,622 A | 5/1994 | Casscells et al. | |
| 5,439,818 A | 8/1995 | Fiddes et al. | |
| 5,478,804 A | 12/1995 | Calabresi et al. | |
| 5,514,566 A | 5/1996 | Fiddes et al. | |
| 5,576,288 A | 11/1996 | Lappi et al. | |
| 5,604,293 A | 2/1997 | Fiddes et al. | |
| 5,679,637 A | 10/1997 | Lappi et al. | |
| 5,916,772 A | 6/1999 | Lappi et al. | |
| 5,919,702 A | 7/1999 | Purchio et al. ................. 435/378 |
| 5,989,866 A | 11/1999 | Deisher et al. ............... 435/69.4 |
| 6,013,477 A | 1/2000 | Greene et al. | |
| 6,054,122 A | 4/2000 | MacPhee et al. | |
| 6,171,340 B1 | 1/2001 | McDowell ................. 623/18.11 |
| 6,200,606 B1 | 3/2001 | Peterson et al. .............. 424/574 |
| 6,221,854 B1 | 4/2001 | Radomsky | |
| 6,352,971 B1 | 3/2002 | Deisher et al. ..................... 514/2 |
| 6,358,971 B1 | 3/2002 | Ezquerra-Carrera et al. | |
| 6,395,921 B1 | 5/2002 | Marhold et al. | |
| 6,518,236 B1 | 2/2003 | Deisher et al. ..................... 514/2 |
| 6,677,321 B1 | 1/2004 | Levin ............................ 514/154 |
| 6,733,753 B2 | 5/2004 | Boone et al. | |
| 7,009,039 B2 | 3/2006 | Yayon et al. | |
| 7,067,144 B2 | 6/2006 | Demopulos et al. | |
| 7,135,459 B2 | 11/2006 | Deisher et al. ................. 514/12 |
| 7,247,608 B2 | 7/2007 | Deisher et al. | |
| 7,470,665 B2 | 12/2008 | West et al. | |
| 7,563,438 B2 | 7/2009 | Deisher et al. | |
| 7,671,020 B2 | 3/2010 | Deisher et al. | |
| 7,745,138 B2 | 6/2010 | Whitehead | |
| 7,749,965 B2 | 7/2010 | Moore et al. | |
| 2003/0008351 A1 | 1/2003 | Deisher et al. | |
| 2003/0022170 A1 | 1/2003 | Khodadoust | |
| 2004/0136970 A1 | 7/2004 | Ellsworth | |
| 2005/0043234 A1 | 2/2005 | Deisher et al. | |
| 2006/0009389 A1 | 1/2006 | Moore et al. | |
| 2008/0194472 A1 | 8/2008 | Whitsett | |

FOREIGN PATENT DOCUMENTS

| | | |
|---|---|---|
| EP | 0931148 | 3/2006 |
| JP | 6-503359 | 4/1994 |
| JP | 7-82171 | 3/1995 |
| JP | 11332570 | 12/1999 |
| JP | 2002-145797 | 5/2002 |
| WO | WO 90/12597 | 11/1990 |
| WO | WO 97/23510 | 7/1997 |
| WO | WO 98/16644 | 4/1998 |
| WO | 99/27100 | 6/1999 |
| WO | 99/46381 | 9/1999 |
| WO | 00/05369 | 2/2000 |
| WO | 00/56890 | 9/2000 |
| WO | 00/67775 | 11/2000 |
| WO | WO 00/78356 A1 | 12/2000 |
| WO | WO 01/39788 | 6/2001 |
| WO | WO 01/78682 A2 | 10/2001 |
| WO | WO 2004/022718 | 3/2004 |
| WO | WO 2004/032849 | 4/2004 |
| WO | WO 2004/047857 | 6/2004 |

OTHER PUBLICATIONS

Lohmander et al. Intra-articular hyaluronan injections in the treatment of osteoarthritis of the knee: a randomised, double blind, placebo controlled multicentre trial. Hyaluronan Multicentre Trial Group. Ann Rheum Dis. Jul. 1996;55(7):424-31.*
Radomsky et al. Potential role of fibroblast growth factor in enhancement of fracture healing. Clin Orthop Relat Res. Oct. 1998;(355 Suppl):S283-93.*
Meyer et al. Sustained in vivo activity of recombinant human granulocyte colony stimulating factor (rHG-CSF) incorporated into hyaluronan, Journal of Controlled Release, vol. 35, Issue 1, Jul. 1995, pp. 67-72.*
Prisell et al. Evaluation of hyaluronan as a vehicle for peptide growth factors, International Journal of Pharmaceutics, vol. 85, Issues 1-3, Sep. 20, 1992, pp. 51-56.*
Karlsson et al. Comparison of two hyaluronan drugs and placebo in patients with knee osteoarthritis. A controlled, randomized, double-blind, parallel-design multicentre study. Rheumatology (Oxford). Nov. 2002;41(11):1240-8.*
Ohbayashi et al., *J. Biol. Chem*, 273(29):18161-18164, 1998.
Hu et al., *Mol. Cell. Biol.* 18(10):6063-6074, 1998.
Ayala et al., *Modern Genetics*, Benjamin/Cummings Pub. Col., CA, pp. 44, 46 and Glossary, 1984.
Long et al., *Cell Regulation* 2:1081-1095, 1991.
Lifeseq.TM. Clone Information Results Incyte Pharmaceuticals Inc., 1995.

(Continued)

Primary Examiner — David Romeo
(74) Attorney, Agent, or Firm — Nelson Mullins Riley & Scarborough LLP; Jane E. Remillard, Esq.; Jeanne M. DiGiorgio

(57) ABSTRACT

FGF18 is known to stimulate the proliferation of chondrocytes, resulting in increased cartilage formation. When hyaluronic acid is administered in addition to FGF18, the effects on chondrocyte proliferation and production of matrix were found to be greater than administration of FGF18 or hyaluronic acid alone.

6 Claims, No Drawings

(56) References Cited

OTHER PUBLICATIONS

Goldfarb, *Cell Growth and Differentiation* 1:439-445, 1990.
Crossley et al., *Cell* 84:127-136, 1996.
Ngo et al., The Protein Folding Problem and Tertiary Structure, Birkhauser, Boston, pp. 491-495, 1994.
Wells, "Additivity of Mutational Effects in Proteins," *Biochemistry* 29(37):8509-8517, 1990.
Bowie et al., "Deciphering the Message in Protein Sequences: Tolerance to Amino Acid Substitutions," *Science* 247:1306-1310, 1990.
Mikayama, T., "Molecular cloning and functional expression of a cDNA encoding glycosylation-inhibiting factor," *Proc. Natl. Acad. Sci. USA* 90:10056-10060, 1993.
Voet et al., *Biochemistry* 1990, John Wiley & Sons, Inc. pp. 126-128 and 228-234, 1990.
Doerks et al., "Protein annotation: detective work for function prediction," *Trends in Genetics*, 14(6):248-250, 1998.
Mickle et al., *Med Clin North Am* 84(3):597-607, 2000.
Yan et al., *Science* 290:523-527, 2000.
Robson et al., Introduction to Proteins and Protein Engineering. New York, Elsevier, pp. 41, 1986.
Liu et al., *Genes & Development* 16:859-869, 2002.
Ohbayashi et al., *Genes & Development* 16:870-879, 2002.
Whitmore et al., *Cytogenet Cell Genet* 90:231-233, 2000.
Shimoaka et al., "Fibroblast Growth Factor (FGF)-18 is a Potent Regulator of Osteoblasts, Osteoclasts, and Chondrocytes: In Vitro Comparison Study with FGF-2 and FGF-10," ASBMR $22^{nd}$ Annual Meeting vol. 15, Suppl 1, SA132, 2000.
Solursh, "Formation of Cartilage Tissue In Vitro," *J. Cell Biochem* 45:258-260, 1991.
Ellsworth et al., *Osteoarthritis and Cartilage* 10:308-320, 2002.
Kikuchi et al., *Osteoarthritis and Cartilage* 4:99-110, 1996.
Wobig et al. The role of elastoviscosity in the efficacy of viscosupplementation for osteoarthritis of the knww: a comparison of hylan G-F 20 and lower-molecular-weight hyaluronan:, Clin Ter., 21(9) 1549-1562, Sep. 1999.
Shimoaka et al., "Regulation of Osteoblast, Chondrocyte, and Osteoclast Functions by Fibroblast Growth Factor (FGF)-18 in Comparison with FGF-2 and FGF-10," *J. Biol. Chem.* 277:7493-7500 (2002).
U.S. Appl. No. 09/574,750, filed May 18, 2000, Deisher, et al.
U.S. Appl. No. 09/613,708, filed Jul. 11, 2000, Deisher, et al.
U.S. Appl. No. 09/634,318, filed Aug. 9, 2000, Deisher, et al.
Australian Patent Office, Examiner's first report dated Dec. 18, 2009, issued on corresponding Australian Application No. 2005269995.
Chesi, et al., "The t(4;14) Translocation in Myeloma Deregulates Both FGFR3 and a Novel Gene, MMSET, Rsulting in IgH/MMSET Hybrid Transcripts," Blood, Nov. 1, 1998, 92(9), pp. 3025-3034.
Coll-Fresno, et al., "Cytotoxic activity of a diptheria toxin/ FGF6 mitotoxin on human tumour cell lines," Oncogene, Jan. 16, 1997, 14(2), pp. 243-247.
Ellsworth et al., "Fibroblast Growth Factor-18 Reduced Infarct Volumes and Behavioral Deficits After Transient Occlusion of the Middle Cerebral Artery in Rats," Stroke, Jun. 2003, 34(6), pp. 1507-1512.
Ellsworth J. L. et al.: "Fibroblast Growth Factor-18 (FGF 18) Reduces Infarct Volume and Behavioral Deficit After Occlusion of the Middle Cerebral Artery in Rats" BIOSIS, (no month available) 2001, vol. 27, p. 2026.
EP Communication from the Examining Division dated Aug. 20, 2004, in corresponding EP Application No. 97910128.4.
EP Communication from the Examining Division dated Oct. 13, 2003, in corresponding EP Application No. 97910128.4.
Hu et al., "Human fibroblast growth factor-18 stimulates fibroblast cell proliferation and is mapped to chromosome 14p11," Oncogene, Apr. 22, 1999, 18, pp. 2635-2642.
Lappi et al., "Biological and chemical characterization of basic FGF-saporin mitotoxin," Biochemical and Biophysical Research Communications, Apr. 28, 1989, 160(2), pp. 917-923.
Lappi, "Tumor targeting through fibroblast growth factor receptors," Seminars in Cancer Biology, (no month available) 1995, 6, pp. 279-288.
Lin, et al., "Fibroblast growth factor-2-toxin induced cytotoxicity: differential sensitivity of co-cultured vascular smooth muscle cells and endothelial cells," Atherosclerosis, (no month available) 1998, 137, pp. 277-289.
Moore, et al.: "Fibroblast Growth Factor-18 Stimulates Chondrogenesis and Promotes Cartilage Repair in a Rat Model of Injury-Induced Osteoarthritis," Annual Meeting, Orthopaedic Research Society, Mar. 10, 2004 vol. 50, Paper No. 199, 1 page.
Ohbayashi, et al., "Structure and Expression of the mRNA Encoding a Novel Fibroblast Growth Factor, FGF-18," The Journal of Biologial Chemistry, Jul. 17, 1998, 273(29), pp. 18161-18164.
PCT International Preliminary Report on Patentability issued Jan. 9, 2007, in corresponding International Application No. PCT/US2005/023866.
PCT International Preliminary Report on Patentability issued Jun. 13, 2007, in corresponding International Application No. PCT/US2005/045166.
PCT International Search Report mailed Aug. 7, 2001, in corresponding International Application No. PCT/US00/32380.
PCT International Search Report mailed Dec. 21, 2005, in corresponding International Application No. PCT/US2005/023866.
PCT International Search Report mailed Feb. 20, 1998, in corresponding International Application No. PCT/US97/18635.
PCT International Search Report mailed May 8, 2006, in corresponding International Application No. PCT/US2005/045166.
Reifers, et al., "Overlapping and Distinct Functions Provided by fgf17, a New Zebrafish Member of the Fgf8/17/18 Subgroup of Fgfs," Mechanisms of Development, Sep. 3, 2000, 99, pp. 39-49.
Schweigerer, et al., "Basic Fibroblast Growth Factor as Growth Inhibitor for Cultured Human Tumor Cells," Journal of Clinical Investigation, Nov. 1987, 80(5), pp. 1516-1520.
Shimoaka, et al., "Fibroblast Growth Factor (FGF)-18 is a Potent Regulator of Osteoblasts, Osteoclasts, and Chondrocytes: In Vitro Comparison Study with FGF-2 and FGF-10," Journal of Bone and Mineral Research, Sep. 2000, 15, p. S257.
Szebenyi, et al., "Fibroblast Growth Factors as Multifunctional Signaling Factors," International Review of Cytology, Sep. 3, 1998, vol. 85, pp. 45-106.
The Merck Manual of Diagnosis and Therapy, Beers (ed.); Whitehouse Station, N.J. 1999; pp. 466-467.
U.S. Appl. No. 08/951,822: Non-Final Office Action dated Dec. 30, 1998.
U.S. Appl. No. 10/081,347: Final Rejection dated Nov. 22, 2006.
U.S. Appl. No. 10/081,347: Non-Final Office Action dated Mar. 15, 2005.
U.S. Appl. No. 10/081,347: Non-Final Office Action dated Mar. 23, 2004.
Burdick et al., "Hyaluronic Acid Hydrogels for Biomedical Applications", Advanced Healthcare Materials, 2011, 23, H41-H56.
Im et al., "Basic Fibroblast Growth Factor Stimulates Matrix Metalloproteinase-13 via the Molecular Cross-talk between the Mitogen-activated Protein Kinases and Protein Kinase Cσ Pathways in Human Adult Articular Chondrocytes", J. Biol. Chem, Apr. 13, 2007, 282(15), 11110-11121.
Loeser et al., "Basic Fibroblast Growth Factor Inhibits the Anabolic Activity of Insulin-like Growth Factor 1 and Osteogenic Protein 1 in Adult Human Articular Chondrocytes", Arthritis Rheum., Dec. 2005, 52(12), 3910-3917.

* cited by examiner

METHODS FOR ADMINISTERING FGF18

This application is a continuation of U.S. application Ser. No. 10/680,673, filed on Oct. 7, 2003, now abandoned, which claims the benefit of U.S. Provisional Application Ser. No. 60/416,670, filed Oct. 7, 2002, which is herein incorporated by reference.

BACKGROUND OF THE INVENTION

The fibroblast growth factor (FGF) family consists of at least twenty three distinct members (Basilico et al., *Adv. Cancer Res.* 59:115-165, 1992 and Fernig et al., *Prog. Growth Factor Res.* 5 (4):353-377, 1994) which generally act as mitogens for a broad spectrum of cell types. FGF18 was identified as a member of the FGF family which was most closely related to FGF8 and FGF17. Activities associated with FGF18 included stimulation of mesenchymal lineage cells, in particular cardiac myocytes, osteoblasts and chondrocytes (U.S. Pat. No. 6,352,971). FGF18 has binds and activates FGFR4 and the "IIIc" splice variants of FGFR3 and FGFR2. It has been shown that FGFR3 plays a role in bone growth. Mice made homozygous null for the FGFR3 (−/−) resulted in postnatal skeletal abnormalities (Colvin et al., *Nature Genet.* 12:309-397, 1996 and Deng et al., *Cell* 84:911-921, 1996). The mutant phenotype suggests that in normal mice, FGFR-3 plays a role in regulation of chondrocyte cell division in the growth plate region of the bone (Goldfarb, *Cytokine and Growth Factor Rev.* 7(4):311-325, 1996). FGF receptor mutations are also found in human chondrodysplasia and craniosynostosis syndromes (Ornitz and Marie, *Genes and Development* 16: 1446-1465, 2002).

Bone remodeling is the dynamic process by which tissue mass and skeletal architecture are maintained. The process is a balance between bone resorption and bone formation, with two cell types thought to be the major players. These cells are the osteoblast and osteoclast. Osteoblasts synthesize and deposit matrix to become new bone. The activities of osteoblasts and osteoclasts are regulated by many factors, systemic and local, including growth factors.

When bone resorption exceeds bone formation, a net loss in bone results, and the propensity for fractures is increased. Decreased bone formation is associated with aging and certain pathological states. In the U.S. alone, there are approximately 1.5 million fractures annually that are attributed to osteoporosis. The impact of these fractures on the quality of the patient's life is immense. Associated costs to the health care system in the U.S. are estimated to be $5-$10 billion annually, excluding long-term care costs.

Other therapeutic applications for growth factors influencing bone remodeling include, for example, the treatment of injuries which require the proliferation of osteoblasts to heal, such as fractures, as well as stimulation of mesenchymal cell proliferation and the synthesis of intramembraneous bone which have been indicated as aspects of fracture repair (Joyce et al. 36th Annual Meeting, Orthopaedic Research Society, Feb. 5-8, 1990. New Orleans, La.).

Replacement of damaged articular cartilage caused either by injury or disease is a major challenge for physicians, and available treatments are considered unpredictable and effective for only a limited time. Virtually all the currently available treatments for cartilage damage focus on relief of pain, with little or no emphasis on regeneration of damaged tissues. Therefore, the majority of younger patients either do not seek treatment or are counseled to postpone treatment for long as possible. When treatment is required, the standard procedure is a total joint replacement or microfracture, a procedure that involves penetration of the subchondral bone to stimulate fibrocartilage deposition by chondrocytes. While deposition of fibrocartilage is not a functional equivalent of articular cartilage, it is at the present the best available treatment because there has been little success in replacing articular cartilage. Two approaches to stimulating deposition of articular cartilage that are being investigated are: stimulating chondrocyte activity in vivo and ex vivo expansion of chondrocytes and their progenitors for transplantation (Jackson et al., *Arthroscopy: The J. of Arthroscopic and Related Surg.* 12:732-738, 1996). In addition, regeneration or repair of elastic cartilage is valuable for treating injuries and defects to ear and nose. Any growth factor with specificity for chondrocytes lineage cells that stimulates those cells to grow, differentiate or induce cartilage production would be valuable for maintaining, repairing or replacing articular cartilage.

Administration of proteins generally requires a formulation that prolongs the half-life or biological activity of the active protein by increasing the resistance to proteolytic degradation or aggregation. Delivery of a protein therapeutic composition can also be difficult when the site for therapeutic action is preferably limited to a specific location in the body. The present invention provides formulations of FGF18 that will be easier to administer and more effective, and other uses that should be apparent to those skilled in the art from the teachings herein.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "hyaluronic acid" are used herein to include derivatives of hyaluronic acid that include esters of hyaluronic acid, salts of hyaluronic acid and also includes the term hyaluronan. The designation also includes both low and high molecular weight forms of hyaluronans and crosslinked hyaluronans or hylans. Examples of such hyaluronans are Synvisc® (Genzyme Corp. Cambridge, Mass.), ORTHO-VISC® (Anika Therapeutics, Woburn, Mass.), and HYAL-GAN® (Sanofi-Synthelabo Inc., Malvern, Pa.)

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "ortholog" denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part on the discovery that when compositions of FGF18 polypeptides or proteins plus a negatively charged carrier, such as hyaluronic acid, are administered to a synovial joint, the stimulatory effects of the FGF18 are enhanced. Therefore, the present invention is directed to compositions of FGF18 polypeptides or proteins plus negatively charged carriers, in particular hyaluronic acid for stimulating the proliferation of mesenchymal cells, particularly chondrocytes. The compositions are administered intraarticularly to a joint, containing synovial fluid.

The nucleotide sequence of the FGF18 cDNA is described in SEQ ID NO. 1, and its deduced amino acid sequence is described in SEQ ID NO. 2. FGF18 was originally designated zFGF5, and is fully described in commonly assigned U.S. Pat. Nos. 6,352,971 and 5,989,866, both incorporated herein by reference. Analysis of the cDNA encoding a FGF18 polypeptide (SEQ ID NO: 1) revealed an open reading frame encoding 207 amino acids (SEQ ID NO: 2) comprising a mature polypeptide of 180 amino acids (residue 28 to residue 207 of SEQ ID NO: 2).

The mouse FGF18 polynucleotide sequence as shown in SEQ ID NO: 3 and corresponding amino acid sequence as shown in SEQ ID NO: 4 were found to have a high degree of homology to that of the human ortholog. At the amino acid level, the mouse and human polypeptides are approximately 98% identical, with three amino acid changes. Those skilled in the art will recognize that the sequences disclosed in SEQ ID NO: 1 or SEQ ID NO: 3 and SEQ ID NO: 2 and SEQ ID NO: 4 represent a single allele of the human and mouse FGF18 gene and polypeptide, respectively, and that allelic variation and alternative splicing are expected to occur.

Members of the FGF family are characterized by heparin binding domains. A putative heparin-binding domain for FGF18 has been identified in the region of amino acid residue 148 (Gly) to amino acid residue 169 (Gln) of SEQ ID NO: 2 and SEQ ID NO: 4. It is postulated that receptor-mediated signaling is initiated upon binding of FGF ligand complexed with cell-surface heparin sulfate proteoglycans. Many FGF family members can be placed into one of two related families on the basis of their structures and functions. aFGF and bFGF consist of three exons separated by two introns of variable length. FGF-8 consists of five exons, the first three of which correspond to the first exon of aFGF and bFGF. All the known FGF family members are spliced to form single polypeptides.

Analysis of the ligand-receptor complex of FGF18 has demonstrated that FGF18 has specificity for FGFR4 and the "IIIc" splice variants of FGFR3 and FGFR2. FGFR3-IIIc and FGFR2-IIIc have been identified within chondrocytes of cartilage tissue, and in particular, both receptors have been found within human articular cartilage. FGFR3 and FGFR2 have been found in the growth plate of mammals and play important roles in the formation of endochondral and intramembranous bone. In particular, FGFR2 and FGFR3 play important roles in developing endochondral and intramembranous bone, FGFR2 is first expressed in condensing mesenchyme and FGFR3 expression is initiated as chondrocytes differentiate and proliferate. In developing cranial bones, FGFR3 is found in the dura mater and periosteum, whereas FGFR2 is expressed in osteoprogenitor cells at the osteogenic front separating the sutures. FGFR2 is also expressed in traebecular bone. (Ornitz and Marie, ibid., 2002) Previously, it has been shown that FGF18 is a proliferative agent for chondrocytes and osteoblasts, depending upon both the differentiated state of these cell types and the mode of administration. (See, U.S. Pat. Nos. 6,352,971 and 5,989,866; Ellsworth et al. *Osteoarthritis and Cartilage*, 10:308-320, 2002; Shimoaka et al., *J. Bio. Chem.* 277 (9) 7493-500, 2002).

Osteoarthritis causes pain in the joints, is believed to be caused by a deficiency in the production of extracellular matrix including sulfated proteoglycans, hyaluronic acid (HA) and type II collagen. HA is natural high viscosity mucopolysaccharide with alternating, (1-3) glucuronidic and, (1-4) glucosaminidic bonds. It is found in the umbilical cord, in vitreous humor, and synovial fluids. For use in the treatment methods and compositions of the present invention, any source of HA is appropriate, however, recombinantly-produced HA (i.e., protein produced in bacterial, yeast, or mammalian cell culture) may be preferred over isolation from animal or human tissue sources in order to insure purity of the composition. In the connective tissue HA functions as binding and protective agent. HA fractions and salts of HA have been used for treatment of damaged bone joints and osteoarthritis. (See, U.S. Pat. No. 5,925,626; U.S. Pat. No. 5,631,241 and EP 0,939,086.) HA is also used in viscosuregery and viscoupplementation and as an aid in ophthalmic surgery.

HA has been used as a component for therapeutic treatment of a variety conditions, both using the HA as the primary therapeutic and as a component of a therapeutic composition useful for treatment. In experiments done by others, HA scaffolds were used to implant autologous chondrocytes into patients' knees, with data showing that symptomatic and functional improvements results. Raynauld et al. (*Osteoarthritis and Cartilage*, 10(7):506-517, 2002) describe results using an HA formulation in conjunction with appropriate care in which clinically effectiveness for primary and secondary outcomes were improved over appropriate care alone. Generally, primary outcomes can be measured as change in the Western Ontario and McMaster (WOMAC) osteoarthritis index, which is a measurement of pain. Secondary outcomes measures will include functional disability and self-reported quality of life. If the therapeutic outcome includes a disease modifying agent, then joint morphology is a primary outcome variable, as well. (Hochberg et al., *J. of Rhematolog.* 24(4): 792-794, 1997).

U.S. Pat. No. 4,636,524 discloses cross-linked gels of HA, alone and mixed with other hydrophilic polymers and containing various substances or covalently bonded low molecular weight substances and processes for preparing them. These products are useful in numerous applications including cosmetic formulations and as drug delivery systems. HA is known to be a biologically tolerable polymer in the sense that it does not cause any immune or other kind of response when introduced into a human body, the cross-linked HA gels can be used for various medical applications. The cross-linked gels modified with other polymers or low molecular weight substances can be used as drug delivery devices.

Canadian Letters Patent 1,240,929 teaches the combination of chondroitin sulfate compound and a hyaluronate to protect both human and animal cell layers and tissue subject to exposure to trauma.

U.S. Pat. No. 4,851,521 and European Patent Application 0,265,116, both describe HA fractions and cross-linked esters of HA. U.S. Pat. No. 4,851,521 describes esters of HA incorporated into pharmaceutical preparations as the active ingredient and as vehicles for ophthamological medicines for topical use and in suppositories for a systemic effect due to the effect of transcutaneous absorption, such as in suppositories.

U.S. Pat. Nos. 6,221,854 and 5,942,499 C1 (Reexam 4806) describe the use of HA and basic FGF (FGF-2) for the treatment of bone. The patent teaches an injectable mixture that is administered into an orthotopic or intraosseous site of desired bone growth.

In contrast, the FGF18 polypeptide and HA compositions of the present invention provide a method for stimulating the proliferation of chondrocytes, in particular differentiated chondrocytes, capable of inducing specialized cell functions, normally associated with terminally differentiated cells. When a composition of FGF18 and HA was administered locally to articular cartilage, proliferation of the cells and concomitant synthesis of glycosaminoglycans was increased beyond the results seen either with FGF18 alone or HA alone. These results indicate that compositions of FGF18 polypeptides and HA can play a therapeutic role in maintaining or repairing cartilaginous tissue, such as joints damaged by osteoarthritis, rheumatoid arthritis or traumatic injury.

FGF18 has been shown to increase cartilage deposition both in vivo and in vitro. Generation of hyaline cartilage, elastic cartilage, and fibrocartilage are valuable both as a therapeutic and as component for biological matrices. FGF18 and HA compositions will be useful in treating articular cartilage defects in synovial joints that are due to age-related superficial fibrillation, cartilage degeneration due to osteoarthritis, and focal chondral and osteochondral defects due to injury or disease. FGF18 and HA compositions will also be useful for treating joint disease caused by osteochondritis dissecans and degenerative joint disease. In the field of reconstructive and plastic surgery, FGF18 and HA compositions will be useful for autogenous or allogenic cartilage expansion and transfer for reconstruction of extensive tissue defects. Expansions of cells and induction of elastic cartilage production will be useful for generation and repair of ear and nose tissue.

FGF18 compositions can be applied by direct injection into the synovial fluid of the joint or directly into the defect, either alone or complexed with a suitable carrier for extended release of protein. However, when FGF18 polypeptide and HA were delivered directly to the synovial joint, the effects of the compositions to stimulate chondrocytes proliferation exceeded that of FGF18 polypeptide or HA alone.

FGF18 can also be used to expand chondrocyte populations in culture for autogenous or allogenic chondrocyte transplantation and then administered with concurrent treatment consisting of administration of FGF18 polypeptide and HA compositions. In these procedures, for example, chondrocytes can be harvested arthroscopically from an uninjured minor load-bearing area of the damaged joint, and can be cultured in the presence of FGF18 compositions to increase the number of cells prior to transplantation. The expanded cultures will then be admixed with FGF18 polypeptide and HA compositions, and placed in the joint space or directly into the defect. FGF18 and HA compositions can be used in combination with periosteal or perichondral grafts that contain cells that can form cartilage and/or help to hold the transplanted chondrocytes or their precursor cells in place. FGF18 and HA compositions can be used to repair cartilage damage in conjunction with lavage of the joint, stimulation of bone marrow, abrasion arthroplasty, subchondral drilling, or microfracture of the subchondral bone. Additionally, after the growth of cartilage due to the administration of the FGF18 and HA composition, additional surgical treatment may be necessary to suitably contour the newly formed cartilage surface.

The compositions of the present invention provide a method for stimulating chondrocyte proliferation and cartilage production in cartilagenous tissues that have been damaged due to traumatic injury or chondropathy. Of particular importance for treatment are tissues that exhibit articulated surfaces, such as, spine, shoulder, elbow, wrist, joints of the fingers, hip, knee, ankle, and the joints of the feet. Examples of diseases that may benefit from treatment include osteoarthritis, rheumatoid arthritis, other autoimmune diseases, or osteochondritis dessicans. In addition, cartilage malformation is often seen in forms of dwarfism in humans suggesting that FGF18 would be useful in these patients.

FGF18 and HA compositions can be applied by direct injection into the synovial space of the joint, into nearby tissues, or directly into a cartilage defect in combination with a carrier that exhibits a negative charge under physiological conditions. Since FGF18 has an isoelectric point of >9.0, at physiological pH FGF18 exhibits a net positive charge. Thus carrier molecules with an abundance of negative charge may bind FGF18 and enhance its activity. Such carriers include low and high molecular weight hyaluronans, sulfated proteoglycans, B-cyclodextrin tetradecasulphate, hydroxyapatite, alginate microspheres, chitosans, and methylcellulose.

For pharmaceutical use, the compositions of the present invention are formulated for intraarticular administration according to conventional methods. The dosage regiment will be determined using various patient variables (e.g., weight, age, sex), as well as clinical presentation (e.g., extent of injury, site of injury, etc.) In general, pharmaceutical formulations will include a FGF18 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, extend half-life, etc. The FGF18 and HA may be administered separately or in combination as a single composition. Thus, the formulations may be provided as a single formulation or as a multicomponent kit. Methods of formulation are well known in the art and are disclosed, for example, in *Remington's Pharmaceutical Sciences*, Gennaro, ed., Mack Publishing Co., Easton Pa., 1990, which is incorporated herein by reference. Determination of dose is within the level of ordinary skill in the art. The proteins may be administered for acute treatment, over one week or less, often over a period of one to three days or may be used in chronic treatment, over several months or years.

In other embodiments, a pharmaceutical FGF18 and HA composition will comprise a formulation for timed-release of the protein. Time-release formulations generally include a monolithic delivery device comprising biocompatible solutions, gels, pastes, and putties in a matrix, in which the composition is entrapped or dissolved. Release from such a timed-release composition occurs by diffusion through the matrix and/or erosion of the matrix. A reservoir system, where the pharmaceutical composition diffuses through a membrane, may also be used.

Although administration of FGF18 and HA, in a pharmaceutically acceptable admixture, is sufficient to provide the delivery of the chondrogenic peptides of the present method, there may be clinical situations where additional drugs are combined in the admixture. Examples of other drugs which may be clinically indicated include anti-inflammatory drugs such as nonspecific and specific cyclooxygenase-2 inhibitors, non-steriodal and steroidal anti-inflammatory drugs. Some of the nonspecific COX inhibitors that could be used in the present invention include salicylic acid and derivatives, such as aspirin or sulfasalazine, para-aminophenol derivatives, such as acetaminophen, indole and indene acetic acids, such as indomethacin or sulindac, arylprpionic acids, such as ibuprofen, naproxen, or oxaprozin, anthranilic acids, such as mefenamic acid, enolic acids including oxicams, or alkanonoes, such as nabumentone. Specific COX-2 inhibitors would be diaryl-substituted fuanonoes (Refecoxib), diaryl-substituted pyrazoles (Celecoxib), indole acetic acids (Etodolac) and sulfonaildes (Nimesulide). Additionally, steroids, such as dexamethazone, prednisone, triamcinolone, or methylprednisone, are among the drugs that could be used. Other types of drugs suitable for the present invention would be inhibitors of the tumor necrosis factor family, such as Enbrel or TACI-Ig, IL-1 antagonists such as Kinaret, antagonists of IL-18 and IL-15, and immunosuppressive drugs such as cyclosporine. In addition, FGF18 may be administered with inhibitors of the CC (MCP-1, RANTES, MIP-1alpha, and MIP-1beta) and CXC (IL-8 and GRO-alpha) chemokine family.

The invention is further illustrated by the following non-limiting examples.

EXAMPLE 1

Intraarticular Injection of FGF18

FGF18 was lyophilized and reconstituted at the appropriate concentration in either PBS or 0.5% hyaluronan (0.2 um sterile filtered). A single dose of FGF18, vehicle (PBS), hyaluronan or the appropriate combination of FGF18 dissolved in either PBS or 0.5% hyaluronan, contained in a final volume of 5 µl was injected into the intraarticular space of the left stifle (knee) of 10 week old female c57/B16 mice. There were seven animals per group. All dosing was performed under isoflurane anesthesia and 100 µl of buprenorephine was administered upon recovery for analgesia. The animals were sacrificed 2 weeks after dosing and tissues were taken for routine histology.

The following dose groups were used:

| Group | treatment |
|---|---|
| I. | no treatment |
| 2 | PBS |
| 3 | 5 µg FGF18 in PBS |
| 4 | 0.5 µg FGF18 in PBS |
| 5 | 0.05 µg FGF18 in PBS |
| 6 | hyaluronan 0.5% |
| 7 | hyaluronan 0.5% + 5.0 µg FGF18 |
| 8 | hyaluronan 0.5% + 0.5 µg FGF18 |
| 9 | hyaluronan 0.5% + 0.05 µg FGF18 |
| 10 | sham injection |

A dose-dependent increase in cartilage formation was observed following two weeks after injection of FGF18 contained in 0.5% hyaluranon. The effective doses were 0.5 and 5 µg FGF18. Definitive evidence of chondrocyte proliferation was seen in 7/7 animals treated with 5.0 µg FGF18 in 0.5% hyaluronan and in 3/7 mice treated with 0.5 µg FGF18 in 0.5% hyaluronan. The increase in cartilage formation was confined to the margins of the joint in the region of the perichondrium, and did not appear to include the articular surface. Little or no chondrocyte proliferation was seen in any of the other groups. Importantly, neither PBS nor hyaluronan alone had any apparent effects on chondrocyte proliferation. There were no apparent effects on the cartilage proliferation when FGF18 was injected in the absence of carrier. These observations, combined with those made previously, suggests that the progenitor cells in the perichondrium are a primary target for FGF18. The lack of effect on the articular chondrocytes may be due to the failure of the protein to penetrate the intact articular surface because FGF18 will stimulate the growth and proteoglycan synthesis of primary human and porcine articular chondrocytes in vitro.

In addition, FGF18 induced closure and mineralization of the growth plate both in the presence and absence of hyaluranon: closure was seen in 2/4 mice treated with 5.0 µg FGF18 in PBS, 2/6 mice treated with 0.5 µg FGF18 in PBS, and 1/7 animals treated with 0.05 µg FGF18 in PBS. This effect was more pronounced in the presence of hyaluronan with closure seen in 7/7 mice treated with 5.0 µg FGF18 in 0.5% hyaluronan and in 5/7 animals treated with 0.5 µg FGF18 in 0.5% hyaluronan. These data reinforce the conclusion that hyaluranon enhances the activity of FGF18.

Inflammation was minimal and only observed at the highest doses of FGF18 in combination with hyaluranon. No cartilage degradation was observed, an important point since bFGF has been reported to have both anabolic and catabolic effects on cartilage.

Lastly, no significant systemic effects of FGF18 were observed in animals that received 5 µg FGF18 with hyaluranon, either at distant cartilage sites or other tissues. However, some focal closures of the epiphysis were observed in one animal that received HA alone and one animal that received 5 gr FGF18 alone. The significance of these observations is not clear at this time.

EXAMPLE 2

Treatment of Osteoarthritis Model

To evaluate whether FGF18 could generate chondral tissue and reverse cartilage degeneration in a setting of osteoarthritis (OA), OA was induced by creating a meniscal tear in the knee joint of rats. In this model, damage to the meniscus induces progressive cartilage degeneration and osteophyte formation that mimic the changes that occur in spontaneous osteoarthritis.

FGF18 was dissolved in a hyaluronan carrier and was applied to the operated knee by intra-articular injection. The repair of cartilage degeneration was evaluated 3 weeks later. The medial collateral ligament of each rat (n=10 rats per group) was transected and the medial meniscus was cut through the full thickness to simulate a complete tear. Three weeks after surgery, rats received intra-articular injections of either vehicle (0.5% hyaluronan) or vehicle containing $E.$ $coli$-derived recombinant human FGF18 (0.1, 1.0, or 5.0 ug) twice per week for three weeks. Four days after the last injection, the knee joints were harvested, collected into buffered formalin, decalcified, and embedded in paraffin for histology. Frontal sections of the knee joints were stained with toluidine blue to assess formation of chondral tissue. An image of the tibial plateau of each knee was captured using an Optimas image analysis system. Multiple sections of the right knee were analyzed microscopically and scored subjectively for cartilage degeneration (chondrocyte/matrix loss and fibrillation) and chondrophyte formation. Strict attention to zones (outside, middle, and inside thirds of the medial tibial plateau) was adhered to and summed to reflect total severity of tibial degeneration. Micrometer measurements of the total extent of the tibial plateau affected by degeneration, width of tibial lesions that extended >50% of cartilage thickness (Tibial Cartilage Degeneration Width), lesion depth (Depth Ratio), thickness of the medial tibial cartilage to the tidemark, and chondrophyte size and number were assessed. Statistical analysis of histopathologic parameters was done by comparing group means using the two-tailed Student's t-test or by analysis of variance. All injections and scoring were performed by investigators blinded to the treatment groups.

In this rat OA model, the degeneration of cartilage is most severe on the outer two-thirds of the tibial plateau and reaches maximal levels at 3 weeks following the meniscal damage. FGF18 was administered from 3 to 6 weeks following surgery to determine if it could induce repair of the damaged cartilage. Analysis indicated that FGF18 induced a dose-dependent increase in cartilage hypertrophy and overgrowth of new cartilage around the damaged areas as well as normal cartilage in the lateral compartment. Specifically, the highest dose of FGF18 (5 µg) resulted in a 57% decrease (p<0.05) in cartilage degeneration scores for the outer 1/3 of the tibial plateau (Table 1), a 57% reduction (p<0.05) in the width of significant tibial cartilage degeneration (Table 2), and a 46% decrease (p<0.05) in depth ratio for any matrix change (Table 3) as a result of filling of the cartilage defects with repair tissue. In addition, FGF18 produced dose-dependent increases in medial tibial cartilage thickness, from 243±21 to 319±77 µm (Table 4) in rats treated with vehicle or 5.0 µg of FGF18, respectively.

The morphology of the repair tissue ranged from fibrous with proteoglycan deposition to fibrocartilage. Repair tissue appeared to originate from the marginal zone areas and extended across the degraded and sometimes intact surfaces. In nearly all areas, repair tissue appeared to integrate well with the margins of the remaining normal cartilage. Although the morphology of the repair tissue was different from hyaline cartilage, it appeared to effectively fill the defect and there were virtually no degenerative changes. In contrast to the FGF18-treated animals, rats treated with vehicle alone showed no signs of cartilage repair except in rare cases where erosion of the subchondral bone permitted influx of bone marrow stem cells. In addition to FGF18-mediated chondrogenesis, other changes were noted in the FGF18-treated joints. For example, the medial tibia chondrophyte measurement at the 1 or 5 μg doses of FGF18 was increased 50% (Table 5).

These data demonstrate that local delivery of FGF18 in a hyaluronan carrier can increase cartilage formation and can reduce cartilage degeneration scores in a rat model of osteoarthritis.

TABLE 1

FGF18 reduced the medial tibia cartilage degeneration scores.

| Treatment Group | Degeneration Score[1] | Number of rats |
|---|---|---|
| HA alone | 3.23 ± 0.34 | 10 |
| HA + 0.1 ug FGF18 | 2.57 ± 0.39 | 10 |
| HA + 1.0 ug FGF18 | 1.93 ± 0.24 | 10 |
| HA + 5.0 ug FGF18 | 1.4* ± 0.18 | 10 |

[1]Mean ± SE Differences significant,
*p = 0.0008 by ANOVA.

TABLE 2

FGF18 reduced the size of large cartilage lesions in the medial tibia plateau.

| Treatment Group | Significant Tibial Cartilage Degeneration Width (um)[1] | Number of Rats |
|---|---|---|
| HA alone | 576.6 ± 100.4 | 10 |
| HA + 0.1 ug FGF18 | 476.6 ± 95.6 | 10 |
| HA + 1.0 ug FGF18 | 416.8 ± 87.9 | 10 |
| HA + 5.0 ug FGF18 | 246.6* ± 50 | 10 |

[1]Mean ± SE. Differences significant,
*p = 0.015 by Student's t-test; p = 0.067 by ANOVA.

TABLE 3

FGF18 reduced the depth of cartilage lesions in the medial tibia plateau.

| Treatment Group | Depth ratio for any matrix change[1] | Number of rats |
|---|---|---|
| HA alone | 0.45 ± 0.05 | 10 |
| HA + 0.1 ug FGF18 | 0.36 ± 0.04 | 10 |
| HA + 1.0 ug FGF18 | 0.34 ± 0.04 | 10 |
| HA + 5.0 ug FGF18 | 0.24* ± 0.26 | 10 |

[1]Mean ± SD. Differences significant,
*p = 0.012 by ANOVA.

TABLE 4

FGF18 increased the medial tibia cartilage thickness in rats with meniscal tear-induced osteoarthritis.

| Treatment Group | Cartilage thickness[1] (um) | Number of rats |
|---|---|---|
| HA alone | 243.8 ± 6.7 | 10 |
| HA + 0.1 ug FGF18 | 249.2 ± 5.3 | 10 |
| HA + 1.0 ug FGF18 | 276.9 ± 13.5 | 10 |
| HA + 5.0 ug FGF18 | 319.1* ± 124.4 | 10 |

[1]Mean ± SE. Differences significant,
$p < 0.05$ by ANOVA.

TABLE 5

FGF18 increased the size of medial tibia chondrophytes.

| Treatment Group | Chondrophyte size[1] (um) | Number of rats |
|---|---|---|
| HA alone | 602.4 ± 49.1 | 10 |
| HA + 0.1 ug FGF18 | 579.0 ± 34.8 | 10 |
| HA + 1.0 ug FGF18 | 874.9 ± 120.9 | 10 |
| HA + 5.0 ug FGF18 | 913.3 ± 51.9 | 10 |

[1]Mean ± SD. Differences significant,
$p < 0.0005$ by ANOVA.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for reducing cartilage degeneration in a joint of a mammal in need thereof comprising the step of injecting into a synovial joint cavity a pharmaceutically acceptable admixture consisting of FGF18 dissolved in approximately 0.5% of a non-crosslinked high molecular weight hyaluronic acid (HA).

2. A method of repairing cartilaginous tissue in a mammal comprising the steps of injecting into a synovial joint cavity a pharmaceutically acceptable admixture consisting of FGF18 dissolved in approximately 0.5% of a non-crosslinked high molecular weight hyaluronic acid (HA).

3. The method of claim 1 or 2, wherein the joint is damaged by osteoarthritis.

4. The method of claim 1 or 2, wherein the joint is damaged by traumatic injury.

5. The method of claim 1 or 2, further comprising the steps of allowing growth of new cartilage tissue and surgically contouring the new cartilage surface.

6. The method of claim 1 or 2, further comprising the step of administering an anti-inflammatory drug.

* * * * *

UNITED STATES PATENT AND TRADEMARK OFFICE
CERTIFICATE OF CORRECTION

PATENT NO. : 8,507,430 B2  Page 1 of 1
APPLICATION NO. : 12/104285
DATED : August 13, 2013
INVENTOR(S) : Jeff L. Ellsworth It is certified that error appears in the above-identified patent and that said Letters Patent is hereby corrected as shown below:

On the Title Page:

Item (56), References Cited, under OTHER PUBLICATIONS:
 Page 2, Column 1, Wobig et al. reference, line 2, change "knww:" to -- know: --.
 Page 2, Column 1, Chesi et al. reference, line 2, change "Rsulting" to -- Resulting --.
 Page 2, Column 1, Coll-Fresno et al. reference, line 1, change "diptheria" to -- diphtheria --.
 Page 2, Column 2, Ohbayashi et al. reference, line 2, change "Biologial" to -- Biological --.

In the Specification:

Column 12, line 22, in TABLE 4, second column, last line, change "319.1* ± 124.4" to -- 319.1* ± 24.4 --.

Signed and Sealed this
Twelfth Day of August, 2014

Michelle K. Lee
*Deputy Director of the United States Patent and Trademark Office*

SEQUENCE LISTING

<160> NUMBER OF SEQ ID NOS: 4

<210> SEQ ID NO 1
<211> LENGTH: 917
<212> TYPE: DNA
<213> ORGANISM: Homo sapiens
<220> FEATURE:
<221> NAME/KEY: CDS
<222> LOCATION: (1)...(621)

<400> SEQUENCE: 1

```
atg tat tca gcg ccc tcc gcc tgc act tgc ctg tgt tta cac ttc ctg      48
Met Tyr Ser Ala Pro Ser Ala Cys Thr Cys Leu Cys Leu His Phe Leu
1               5                   10                  15 ctg ctg tgc ttc cag gta cag gtg ctg gtt gcc gag gag aac gtg gac      96
Leu Leu Cys Phe Gln Val Gln Val Leu Val Ala Glu Glu Asn Val Asp
            20                  25                  30 ttc cgc atc cac gtg gag aac cag acg cgg gct cgg gac gat gtg agc      144
Phe Arg Ile His Val Glu Asn Gln Thr Arg Ala Arg Asp Asp Val Ser
```

```
                35                  40                  45
cgt aag cag ctg cgg ctg tac cag ctc tac agc cgg acc agt ggg aaa      192
Arg Lys Gln Leu Arg Leu Tyr Gln Leu Tyr Ser Arg Thr Ser Gly Lys
 50                  55                  60 cac atc cag gtc ctg ggc cgc agg atc agt gcc cgc ggc gag gat ggg      240
His Ile Gln Val Leu Gly Arg Arg Ile Ser Ala Arg Gly Glu Asp Gly
 65                  70                  75                  80 gac aag tat gcc cag ctc cta gtg gag aca gac acc ttc ggt agt caa      288
Asp Lys Tyr Ala Gln Leu Leu Val Glu Thr Asp Thr Phe Gly Ser Gln
                 85                  90                  95 gtc cgg atc aag ggc aag gag acg gaa ttc tac ctg tgc atg aac cgc      336
Val Arg Ile Lys Gly Lys Glu Thr Glu Phe Tyr Leu Cys Met Asn Arg
                100                 105                 110 aaa ggc aag ctc gtg ggg aag ccc gat ggc acc agc aag gag tgt gtg      384
Lys Gly Lys Leu Val Gly Lys Pro Asp Gly Thr Ser Lys Glu Cys Val
            115                 120                 125 ttc atc gag aag gtt ctg gag aac aac tac acg gcc ctg atg tcg gct      432
Phe Ile Glu Lys Val Leu Glu Asn Asn Tyr Thr Ala Leu Met Ser Ala
130                 135                 140 aag tac tcc ggc tgg tac gtg ggc ttc acc aag aag ggg cgg ccg cgg      480
Lys Tyr Ser Gly Trp Tyr Val Gly Phe Thr Lys Lys Gly Arg Pro Arg
145                 150                 155                 160 aag ggc ccc aag acc cgg gag aac cag cag gac gtg cat ttc atg aag      528
Lys Gly Pro Lys Thr Arg Glu Asn Gln Gln Asp Val His Phe Met Lys
                165                 170                 175 cgc tac ccc aag ggg cag ccg gag ctt cag aag ccc ttc aag tac acg      576
Arg Tyr Pro Lys Gly Gln Pro Glu Leu Gln Lys Pro Phe Lys Tyr Thr
            180                 185                 190 acg gtg acc aag agg tcc cgt cgg atc cgg ccc aca cac cct gcc          621
Thr Val Thr Lys Arg Ser Arg Arg Ile Arg Pro Thr His Pro Ala
        195                 200                 205 taggccaccc cgccgcggcc ctcaggtcgc cctggccaca ctcacactcc cagaaaactg    681
catcagagga atattttac atgaaaaata aggattttat tgttgacttg aaaccccga     741 tgacaaaaga ctcacgcaaa gggactgtag tcaacccaca ggtgcttgtc tctctctagg    801
aacagacaac tctaaactcg tccccagagg aggacttgaa tgaggaaacc aacactttga    861
gaaaccaaag tccttttcc caaaggttct gaaaaaaaaa aaaaaaaaaa ctcgag          917
```

<210> SEQ ID NO 2
<211> LENGTH: 207
<212> TYPE: PRT
<213> ORGANISM: Homo sapiens

<400> SEQUENCE: 2

```
Met Tyr Ser Ala Pro Ser Ala Cys Thr Cys Leu Cys Leu His Phe Leu
 1               5                  10                  15

Leu Leu Cys Phe Gln Val Gln Val Leu Val Ala Glu Glu Asn Val Asp
            20                  25                  30

Phe Arg Ile His Val Glu Asn Gln Thr Arg Ala Arg Asp Asp Val Ser
         35                  40                  45

Arg Lys Gln Leu Arg Leu Tyr Gln Leu Tyr Ser Arg Thr Ser Gly Lys
 50                  55                  60

His Ile Gln Val Leu Gly Arg Arg Ile Ser Ala Arg Gly Glu Asp Gly
 65                  70                  75                  80

Asp Lys Tyr Ala Gln Leu Leu Val Glu Thr Asp Thr Phe Gly Ser Gln
                 85                  90                  95

Val Arg Ile Lys Gly Lys Glu Thr Glu Phe Tyr Leu Cys Met Asn Arg
                100                 105                 110
```

```
Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Pro Glu Leu Gln Lys Pro Phe Lys Tyr Thr
            180                 185                 190

Thr Val Thr Lys Arg Ser Arg Arg Ile Arg Pro Thr His Pro Ala
            195                 200                 205

<210> SEQ ID NO 3
<211> LENGTH: 1023
<212> TYPE: DNA
<213> ORGANISM: Mus musculus
<220> FEATURE:
<221> NAME/KEY: CDS
<222> LOCATION: (1)...(624)

<400> SEQUENCE: 3 atg tat tca gcg ccc tcc gcc tgc act tgc ctg tgt tta cac ttt cta      48
Met Tyr Ser Ala Pro Ser Ala Cys Thr Cys Leu Cys Leu His Phe Leu
1               5                   10                  15 ctg ctg tgc ttc cag gtt cag gtg ttg gca gcc gag gag aat gtg gac      96
Leu Leu Cys Phe Gln Val Gln Val Leu Ala Ala Glu Glu Asn Val Asp
            20                  25                  30 ttc cgc atc cac gtg gag aac cag acg cgg gct cga gat gat gtg agt     144
Phe Arg Ile His Val Glu Asn Gln Thr Arg Ala Arg Asp Asp Val Ser
        35                  40                  45 cgg aag cag ctg cgc ttg tac cag ctc tat agc agg acc agt ggg aag     192
Arg Lys Gln Leu Arg Leu Tyr Gln Leu Tyr Ser Arg Thr Ser Gly Lys
    50                  55                  60 cac att caa gtc ctg ggc cgt agg atc agt gcc cgt ggc gag gac ggg     240
His Ile Gln Val Leu Gly Arg Arg Ile Ser Ala Arg Gly Glu Asp Gly
65                  70                  75                  80 gac aag tat gcc cag ctc cta gtg gag aca gat acc ttc ggg agt caa     288
Asp Lys Tyr Ala Gln Leu Leu Val Glu Thr Asp Thr Phe Gly Ser Gln
                85                  90                  95 gtc cgg atc aag ggc aag gag aca gaa ttc tac ctg tgt atg aac cga     336
Val Arg Ile Lys Gly Lys Glu Thr Glu Phe Tyr Leu Cys Met Asn Arg
            100                 105                 110 aaa ggc aag ctc gtg ggg aag cct gat ggt act agc aag gag tgc gtg     384
Lys Gly Lys Leu Val Gly Lys Pro Asp Gly Thr Ser Lys Glu Cys Val
        115                 120                 125 ttc att gag aag gtt ctg gaa aac aac tac acg gcc ctg atg tct gcc     432
Phe Ile Glu Lys Val Leu Glu Asn Asn Tyr Thr Ala Leu Met Ser Ala
130                 135                 140 aag tac tct ggt tgg tat gtg ggc ttc acc aag aag ggg cgg cct cgc     480
Lys Tyr Ser Gly Trp Tyr Val Gly Phe Thr Lys Lys Gly Arg Pro Arg
145                 150                 155                 160 aag ggt ccc aag acc cgc gag aac cag caa gat gta cac ttc atg aag     528
Lys Gly Pro Lys Thr Arg Glu Asn Gln Gln Asp Val His Phe Met Lys
                165                 170                 175 cgt tac ccc aag gga cag gcc gag ctg cag aag ccc ttc aaa tac acc     576
Arg Tyr Pro Lys Gly Gln Ala Glu Leu Gln Lys Pro Phe Lys Tyr Thr
            180                 185                 190 aca gtc acc aag cga tcc cgg cgg atc cgc ccc act cac ccc ggc tag     624
Thr Val Thr Lys Arg Ser Arg Arg Ile Arg Pro Thr His Pro Gly *
            195                 200                 205
```

-continued

```
                195                 200                 205
gtccggccac actcaccccc ccagagaact acatcagagg aatattttta catgaaaaat        684
aaggaagaat ctctattttt gtacattgtg tttaaaagaa gacaaaaact gaacctaaag        744
tcttgggagg aggggcgata ggattccact gttgacctga accccatgac aaaggactca        804
cacaagggga ccgctgtcaa cccacaggtg cttgcctctc tctaggaggt gacaattcaa        864
aactcatccc cagaggagga cttgaacgag gaaactgcga gaaaccaaag tcctttcccc        924
ccaaaggttc tgaaagcaaa caaaaaaaaa aaaaaaaaa aaaaaaaaa aaaaaaaaa          984 aaaaaaaaaa aaaaaaaaaa gggcggccgc tctagagga                             1023
```

<210> SEQ ID NO 4
<211> LENGTH: 207
<212> TYPE: PRT
<213> ORGANISM: Mus musculus

<400> SEQUENCE: 4

```
Met Tyr Ser Ala Pro Ser Ala Cys Thr Cys Leu Cys Leu His Phe Leu
  1               5                  10                  15

Leu Leu Cys Phe Gln Val Gln Val Leu Ala Ala Glu Glu Asn Val Asp
             20                  25                  30

Phe Arg Ile His Val Glu Asn Gln Thr Arg Ala Arg Asp Asp Val Ser
         35                  40                  45

Arg Lys Gln Leu Arg Leu Tyr Gln Leu Tyr Ser Arg Thr Ser Gly Lys
     50                  55                  60

His Ile Gln Val Leu Gly Arg Arg Ile Ser Ala Arg Gly Glu Asp Gly
 65                  70                  75                  80

Asp Lys Tyr Ala Gln Leu Leu Val Glu Thr Asp Thr Phe Gly Ser Gln
                 85                  90                  95

Val Arg Ile Lys Gly Lys Glu Thr Glu Phe Tyr Leu Cys Met Asn Arg
            100                 105                 110

Lys Gly Lys Leu Val Gly Lys Pro Asp Gly Thr Ser Lys Glu Cys Val
        115                 120                 125

Phe Ile Glu Lys Val Leu Glu Asn Asn Tyr Thr Ala Leu Met Ser Ala
    130                 135                 140

Lys Tyr Ser Gly Trp Tyr Val Gly Phe Thr Lys Lys Gly Arg Pro Arg
145                 150                 155                 160

Lys Gly Pro Lys Thr Arg Glu Asn Gln Gln Asp Val His Phe Met Lys
                165                 170                 175

Arg Tyr Pro Lys Gly Gln Ala Glu Leu Gln Lys Pro Phe Lys Tyr Thr
            180                 185                 190

Thr Val Thr Lys Arg Ser Arg Arg Ile Arg Pro Thr His Pro Gly
        195                 200                 205
```